United States Patent
Sawicki

(10) Patent No.: US 6,506,948 B1
(45) Date of Patent: Jan. 14, 2003

(54) TOLUENE EXTRACTION OF DINITROTOLUENE WASH WATER

(75) Inventor: John Edward Sawicki, Breinigsville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/072,217

(22) Filed: Feb. 7, 2002

(51) Int. Cl.$^7$ .............................................. C07C 205/00
(52) U.S. Cl. ........................ 568/934; 568/927; 568/939; 568/940
(58) Field of Search ................. 568/934, 927, 568/939, 940

(56) References Cited

U.S. PATENT DOCUMENTS

| | | | |
|---|---|---|---|
| 4,241,229 A | 12/1980 | Alexanderson | 568/939 |
| 4,257,986 A | 3/1981 | Milligan et al. | 568/934 |
| 4,597,875 A * | 7/1986 | Carr et al. | 210/710 |
| 4,642,396 A | 2/1987 | Carr et al. | 568/934 |
| 4,650,912 A * | 3/1987 | Pohl et al. | 568/934 |

* cited by examiner

*Primary Examiner*—Jafar Parsa
(74) *Attorney, Agent, or Firm*—Mary E. Bongiorno

(57) ABSTRACT

This invention relates to an improvement in a process for the production of dinitrotoluene and particularly to the recovery of dinitrotoluene and organic by-products from the wastewater and wash waters generated in the process. Wastewater and wash water streams contaminated with residual levels of mononitrotoluene, dinitrotoluene, and organic by-products, formed in the purification process, are contacted with toluene. An organic phase and an aqueous phase are generated. The phases are separated and the dinitrotoluene recovered from the organic phase.

8 Claims, 3 Drawing Sheets

THREE STAGE TOLUENE EXTRACTION

TOLUENE EXTRACTION OF DINITROTOLUENE WASH WATER

BACKGROUND OF THE INVENTION

Nitroaromatic compositions have been widely used as intermediates in the chemical industry and are well suited for producing a variety of industrial chemicals such as aromatic amines. Nitration of aromatic hydrocarbons is effected commercially by the mixed acid method wherein the aromatic compound is contacted with a concentrated mixture of sulfuric acid and nitric acid. Subsequent to nitration an organic layer containing the desired nitration product and an aqueous spent acid layer is formed. These layers are separated and the nitroaromatic product recovered.

A major problem in the industry associated with the production of dinitrotoluene (DNT) is that of wastewater and wash water treatment. Prior to discharge these wastewater and wash water streams generated from multiple water and aqueous acid wash steps and from water of reaction require removal of the byproducts, such as, picric acid, nitrocresols, nitrophenols, as well as acids and so forth. The removal problem is significantly more severe with dinitration processes than with mononitration processes.

Representative patents which pertain to the nitration of aromatic compounds, including the nitration of toluene and the treatment of wash water streams generated in these processes are as follows:

U.S. Pat. No. 4,642,396 discloses a process for recovering nitric acid from the nitration medium which contains unreacted aromatic compound, nitroaromatic dissolved in nitric acid and water. The process involves treating the spent acid containing nitric acid with nitric oxide under conditions for generating nitrogen dioxide and water. The nitrogen dioxide is removed from the reaction medium as a gas. It is subsequently oxidized to nitric acid. The nitroaromatic compound is forced into the organic layer because of the reduced concentration of nitric acid and recovered therefrom.

U.S. Pat. No. 4,241,229 discloses a process for the recovery of nitroaromatic compounds from wastewater and wash waters in a mixed acid nitration process. In the nitration of benzene, it had been common practice to strip the wash liquors with steam. Steam stripping was deemed costly in terms of equipment and energy. The patentees suggested contacting the wash liquor with the aromatic compound being nitrated and recycling the resulting solution to the nitration reaction.

U.S. Pat. No. 4,257,986 discloses a process for the manufacture of dinitrotoluene by the mixed acid technique. The improvement in the process resides in contacting the spent acid with feed aromatic compound to remove contaminant organics and residual nitric acid. There is also disclosed an extraction process wherein denitrated acid is contacted with crude dinitrotoluene to remove substantially all of the residual nitric acid dissolved in the dinitrotoluene. Residual toluene is removed by air sparging or solvent extraction with butane.

BRIEF SUMMARY OF THE INVENTION

This invention relates to a multi-step process for the removal of nitrotoluenes from the wastewaters and wash waters generated in the mixed acid dinitration of toluene. In the basic process for the production of dinitrotoluene, toluene is contacted with a mixture of nitric and sulfuric acid under conditions for effecting dinitration. Generally, three wastewater and wash water streams contaminated with residual levels of mononitrotoluene, dinitrotoluene and organic byproducts are generated. One wastewater stream is generated from the steam stripping of nitric acid and organics from spent acid, the distillate, and, herein, referred to as "weak acid wastewater"; another stream is generated from washing the dinitrotoluene reaction product, herein referred to as "acid wash water"; and one stream results from alkaline washing of the dinitrotoluene reaction product, herein referred to as "alkaline wash water". The improvement for effecting recovery of dinitrotoluene from the wastewater and wash water streams and effecting a purification of the wash water streams for subsequent disposal comprises the steps:

(a) initially extracting the residual levels of mononitrotoluene, dinitrotoluene and organic byproducts from at least one of the weak acid wastewater stream and acid wash water streams by contacting at least one stream with toluene and thereby generating an organic phase and an aqueous phase;

(b) separating the thus formed organic phase from the aqueous phase;

(c) extracting residual levels of mononitrotoluene, dinitrotoluene and organic byproducts from the alkaline wash water stream by contacting said stream with the organic phase generated in step (a) and thereby generating a toluene/dinitrotoluene organic layer and an extracted alkaline wash water fraction; and, (d) separating the toluene/dinitrotoluene organic layer from the extracted alkaline wash water fraction.

There are advantages that may be obtained by the process depending upon which embodiments are employed; they include:

an ability to extract 99+% of the dinitrotoluene and mononitrotoluene in two or three extraction stages and isolate most of the impurities in a single stream so that they can be efficiently destroyed chemically, physically or biologically without the complicating factor of having large amounts of dinitrotoluene interfere with the destruction process; and, an ability to recover virtually all of the dinitrotoluene that was formerly wasted or destroyed.

DETAILED DESCRIPTION OF THE INVENTION

Figure 1:
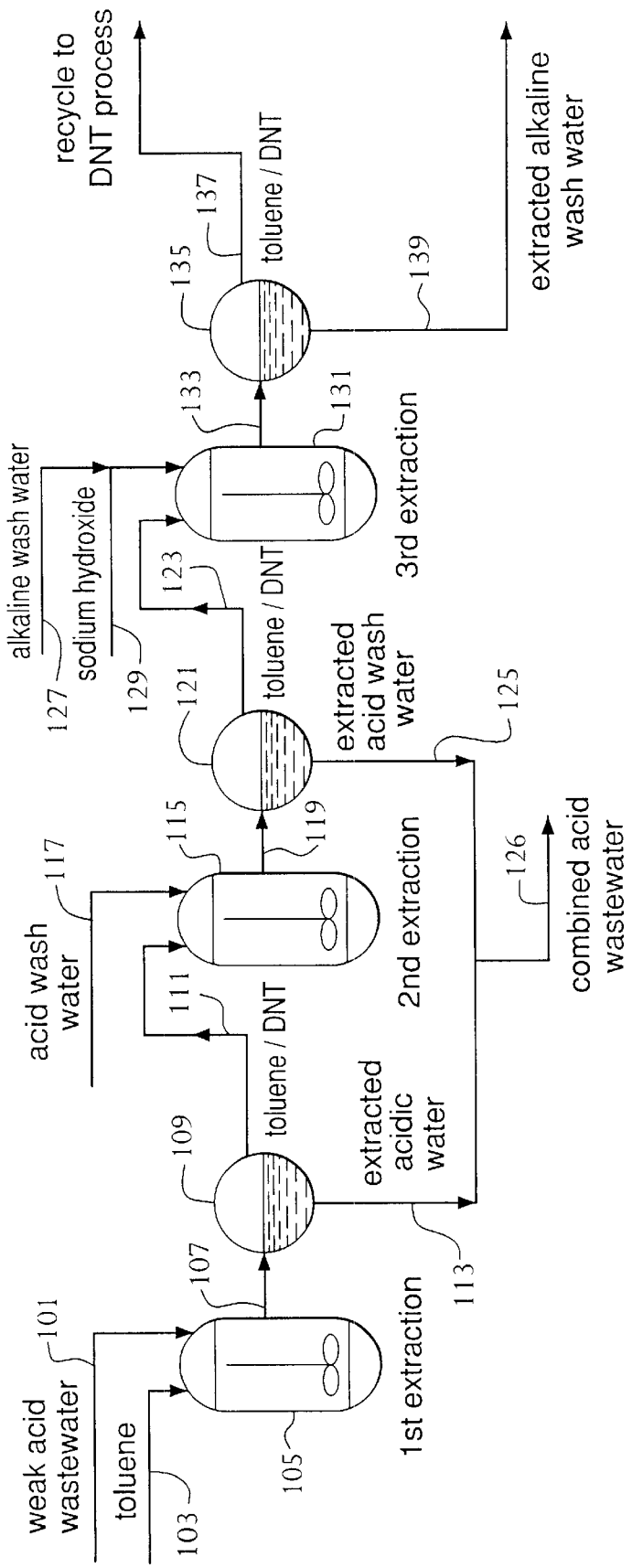
FIG. 1 is a flow diagram of a three-stage process for effecting toluene extraction of the wastewaters and wash waters generated in a dinitrotoluene process.

In a commercial process for the synthesis of dinitrotoluene (DNT) by the mixed acid technique, toluene is initially converted to mononitrotoluene (MNT) in a first stage, the reaction mixture separated into an organic phase containing mononitrotoluene and an aqueous phase containing spent sulfuric acid minor traces of nitric acid and organic byproducts. Then, the MNT is converted to DNT in a second stage.

The dinitration reaction product is separated into an organic phase containing dinitrotoluene and an aqueous phase containing spent sulfuric acid.

In the mixed acid process, the reaction media is a mixture of nitric and sulfuric acids. Nitric acid is a reactant and is depleted in the chemical reaction. Sulfuric acid is not consumed in the process but it is, however, diluted with water of reaction and with any water present in the feeds. The resulting spent nitric acid/sulfuric acid from the dinitration process is stripped of the residual nitric acid and dissolved and entrained organics and the sulfuric acid recovered and concentrated for reuse.

In many commercial dinitration processes, there are three water streams that are generated and have interest here. One stream is referred to as the "weak acid wastewater" stream. It is generated as follows. Prior to the concentration of the spent sulfuric acid, the spent sulfuric acid containing residual levels of nitric acid and organics is steam stripped. The water, i.e.; the distillate recovered from after steam stripping is contaminated with nitric acid and organic compounds, primarily MNT and DNT as well as small amounts of organic byproducts and entrained sulfuric acid. The primary organic byproducts include phenol, nitrophenols, dinitrophenols, cresols, dinitrocresols and trinitrocresols as well as trace quantities of other unidentified organic compounds. The total concentration of organic byproducts in the DNT wash water is in the 1,000–3,000 ppm (0.1–0.3 wt %) range.

A second stream often referred to as the "acid wash water" is generated in the washing of the organic phases generated in the dinitration process. Although the MNT and DNT yields in the separate phases are very high (99+%), oxidative organic byproducts (impurities) are also produced. In the washing step, entrained and soluble mineral acids (sulfuric and nitric acids) are removed by contacting the "raw" DNT recovered from the dinitration zone with essentially clean water. This wash water is contaminated and sometimes saturated with DNT and it contains mineral acids and some impurities. It is separated from the organic phase which is referred to as "water washed DNT".

The third stream is referred to as "alkaline wash water" and is generated by alkaline treatment of water washed dinitrotoluene. More specifically, the water washed DNT is contacted with a weak aqueous solution of appropriate base to remove most of the impurities that are acidic and any organics that can be converted to water-soluble salts. These salts then partition into the water phase. Bases suited for removal of impurities include: sodium hydroxide, sodium carbonate, and ammonia (ammonium hydroxide). After contacting DNT with an aqueous basic solution the organic phase and the aqueous phase are separated. The resulting toluene/DNT organic phase is recovered. The alkaline wash water often is pretreated to remove some of the impurities before disposal. In most cases the alkaline wash water is chemically (oxidation) or physically (adsorption) treated before discharging into a final biological treatment process. Depending on the ratio of alkaline water to DNT, the alkaline wash water contains between 1,000 and 10,000 ppm (0.1–1.0 wt %) of the impurities.

The three wastewater and wash water streams described above constitute the bulk of the wastewater and wash waters emanating from the dinitration process. The volumes of these streams are not equal and vary with the operation (i.e. the degree of recycling wash water or the aqueous to organic ratios can change and, therefore, wastewater and wash water streams may vary). Heretofore, conventional operation did not attempt to recover the residual organic compounds (primarily MNT and DNT) from the wastewater and wash water streams because of their relatively low concentrations.

Figure 2:
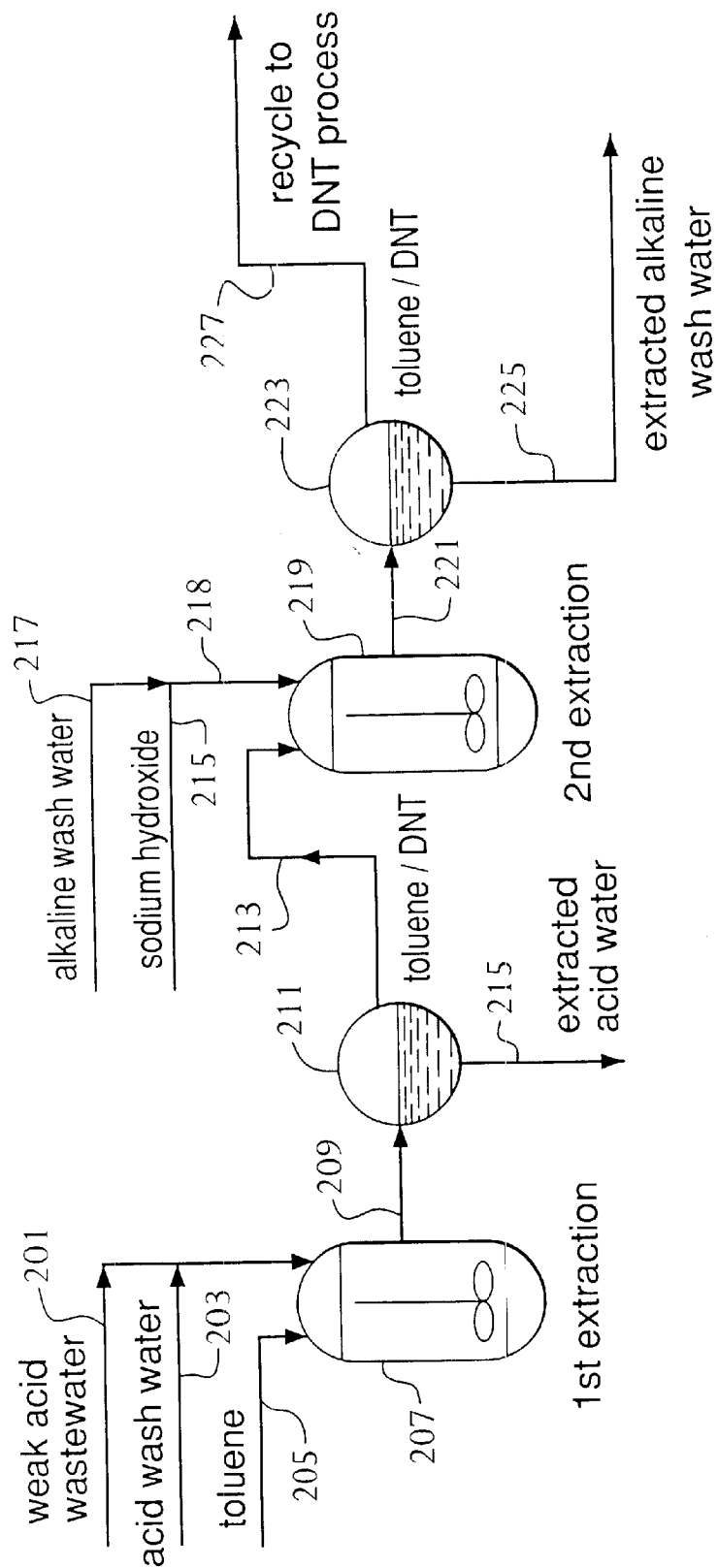
FIG. 2 is a flow diagram of a two-stage process for effecting toluene extraction of the wastewater and wash waters generated in a dinitrotoluene process.
Figure 3:
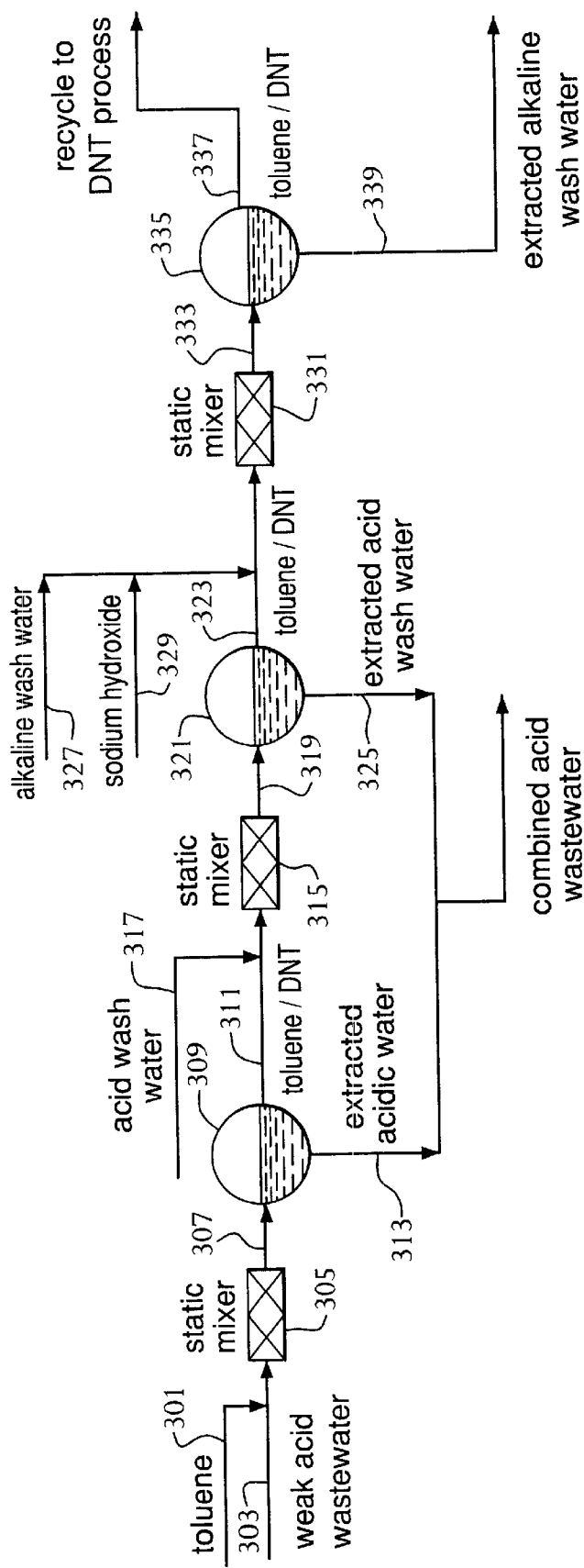
FIG. 3 is a flow diagram of a three-stage process for effecting toluene extraction of the wastewater and wash waters generated in a dinitrotoluene process including inline static mixers.

To facilitate an understanding of the recovery process of the invention, reference is made to FIGS. 1–3. Toluene is added to the process in proportion to the volume of the combined wastewater and wash water streams and, initially, to the largest acidic stream. It has been found that an approximate ratio of slightly >0.1 (toluene:wastewater/wash water, by volume) is desirable because it provides excellent extraction efficiency and the volume is small with respect to the total toluene used in the nitration process. This ratio can range from 0.1 to 2.5 volume parts toluene per volume part total wastewater and wash water with the preferred range being from 0.2–0.6 volume parts toluene per volume part total wastewater and wash water.

In FIG. 1, weak acid wastewater, which is the largest acidic wash water stream, and toluene are introduced via lines 101 and 103 respectively to stirred tank 105. In tank 105 the weak acid wastewater and toluene are thoroughly mixed and then conveyed via line 107 to phase separator 109. The aqueous phase and organic phase are allowed to separate and the organic phase containing a mixture of toluene, residual dinitrotoluene and organic byproducts are removed via line 111 while the aqueous phase is removed via line 113. Sometimes this step may be eliminated and the recovery allowed to proceed to the second extraction described below.

The toluene/DNT mixture in line 111 is introduced to a second stirred tank 115 and mixed with acid wash water. The streams are thoroughly mixed in stirred tank 115, removed via line 119 and separated in phase separator 121. The organic phase containing most of the MNT and DNT, and some of the byproducts from the two streams, is removed via line 123 and the aqueous phase is removed via line 125. The aqueous phase in line 113 is combined with the aqueous phase in line 125 and sent for further processing via line 126.

A third extraction is shown in the process of FIG. 1 in that alkaline wash water, and sodium hydroxide are conveyed via lines 127 and 129, respectively, to a third stirred tank extractor 131 and mixed. Because the toluene from the first two extractions contains high levels of MNT and DNT, adjustment of the pH to about a level of from 7 to 10, preferably 8–9 is a preferred step. The pH adjustment prevents undesirable byproducts from being extracted into the toluene/DNT product and removed therewith via line 137 on phase separation. In the preferred case, then, the alkaline wash water introduced via line 127 can be used to extract byproducts from the toluene, thereby "cleaning" it up and making it suitable for recycling to the DNT process.

A final extraction stream is removed via line 133 and the mixture separated in phase separator 135. The resulting toluene/DNT mixture free of contaminant organic byproducts, is removed from phase separator 135 and conveyed via line 137 to the feed inlet line in the dinitration process or destroyed. The aqueous phase comprised of extracted alkaline wash water free of residual DNT but containing solubilized organic byproducts is removed via line 139 and sent to discharge for subsequent treatment.

FIG. 2 illustrates a two-step extraction process instead of the three-step process described in FIG. 1. Weak acid wastewater, acid wash water and toluene are introduced via lines 201, 203 and 205 to first stirred tank 207. As in FIG. 1, the streams are mixed at levels to provide a toluene/water volume ratio of about 0.20. The mixture of toluene and wash water is removed via line 209 and introduced to phase separator 211 wherein a toluene/DNT organic phase is removed via line 213 and an extracted acid water phase is removed via line 215. Sodium hydroxide and alkaline wash water are introduced via lines 215 and 217 into a common line 218 and then to second stirred tank 219. The toluene/DNT fraction in line 213 is mixed with the sodium hydroxide and alkaline wash water introduced via line 218. A mixture comprised of an organic phase and water is removed via line 221 and sent to phase separator 223. An aqueous extracted alkaline wash water fraction is removed via line 225 and a product toluene/DNT organic phase containing most of the MNT and DNT and substantially free of residual organic byproducts is removed via line 227. As in the process described in FIG. 1, the pH adjustment at this stage prevents many undesirable organic byproducts from being extracted on separation into the toluene/DNT product in line 227. In the preferred case, then, the alkaline wash water introduced via line 217 can be used to extract byproducts from the toluene, thereby "cleaning" it up and making it suitable for recycling to the DNT process.

FIG. 3 is a variation on the embodiment of FIG. 1. Inline (static) mixers are employed to replace the stirred tank extractors 105, 115, and 131, respectively. For purposes of FIG. 3, a three hundred series has been used to correspond to the 100 series used in FIG. 1. The use of inline static mixers allows one to simplify the process and reduce capital expenditure.

Static mixers suited for the mixing of toluene and the wastewater and wash water streams are known and are typically comprised of parallel plates interposed at an angle to each other. More particularly, they are comprised of a plurality of sections comprised of a tubular housing having a flow direction along an axis carrying stationary, rigid elements that form interengaging and intersecting channels in the flow direction. These channels define a tortuous pathway from inlet to outlet of the tubular housing. This pathway is designed so that the interengaging and intersecting channels effect a splitting of the fluid streams, a rearranging of the fluid streams and then a combining of these streams as the fluids pass through the tubular housing. The angles at which the alternating parallel channels intersect may vary but typically such angles are within a range of from 45 to 90 degrees.

One type of static mixer is comprised of a tubular housing having a wall, an axis and a flow direction, the axis dividing the interior of the housing into longitudinally extending first and second interior housing sectors. A mixing element includes at least two mixing sections with one of the sections disposed in a housing sector. The flow direction in the mixing sections are defined by parallel, spaced apart strips extending in the flow direction nonparallel to the housing axis. Once the fluid contacts the wall surface it is allowed to flow upward to the next parallel strip and directed in an opposite flow nonparallel to the axis.

The following examples are provided to illustrate various embodiments of the invention and are not intended to restrict the scope thereof.

EXAMPLE 1

Evaluation of Toluene/Wash Water Ratios

Several sets of experiments were conducted to determine the desirable toluene/water volume ratios for extracting MNT and DNT from DNT wastewater and wash waters containing residual MNT, DNT and organic byproducts and residual acid.

Aqueous wash water streams from a DNT process were extracted with toluene in an effort to remove MNT and DNT. For this series of tests, samples of alkaline wash water, acid wash water, and weak acid wastewater were individually mixed with toluene for five (5) minutes and, after phase separation, the water phase analyzed for DNT, MNT and byproducts. Test toluene:wastewater and wash water volume ratios were 0.13, 0.60, 1.1 and 2.4 by volume and temperature was maintained at 50° C. (112° F.). Table A–D provide the results.

| Weak Acid Wastewater Extraction Starting Concentrations in Water | |
|---|---|
| Compound | mg/l |
| MNT | 93 |
| DNT | 1464 |
| Cresols | 6 |
| Unknown | 43 |

TABLE A

Toluene/water = 0.12 by volume
(toluene = 12.3 ml, water = 100.5 ml)

| Extracted water | | | Concentrations in toluene (calculated) | |
|---|---|---|---|---|
| Compound | mg/l | % Extracted | Compound | mg/l |
| MNT | 0 | 100 | MNT | 760 |
| DNT | 21 | 98.6 | DNT | 11790 |
| cresols | 3 | 50.0 | Cresols | 25 |
| unknown | 30 | 30.2 | unknown | 106 |

TABLE B

Toluene/water = 0.60 by volume
(toluene = 40.0 ml, water = 69.9 ml)

| Extracted water | | | Concentrations in toluene (calculated) | |
|---|---|---|---|---|
| Compound | mg/l | % Extracted | Compound | mg/l |
| MNT | 0 | 100 | MNT | 156 |
| DNT | 0 | 100 | DNT | 2449 |
| cresols | 1 | 83.3 | cresols | 8 |
| unknown | 42 | 2.3 | unknown | 2 |

TABLE C

Toluene/water = 1.19 by volume
(toluene = 60.1 ml, water = 50.5 ml)

| Extracted water | | | Concentrations in toluene (calculated) | |
|---|---|---|---|---|
| Compound | mg/l | % Extracted | Compound | mg/l |
| MNT | 0 | 100 | MNT | 78 |
| DNT | 0 | 100 | DNT | 1230 |
| cresols | 2 | 66.7 | cresols | 3 |
| unknown | 13 | 69.8 | unknown | 25 |

TABLE D

Toluene/water = 2.43 by volume
(toluene = 87.8 ml, water = 36.2 ml)

| | Extracted water | | Concentrations in toluene (calculated) | |
|---|---|---|---|---|
| Compound | mg/l | % Extracted | Compound | mg/l |
| MNT | 0 | 100 | MNT | 38 |
| DNT | 0 | 100 | DNT | 604 |
| cresols | 2 | 66.7 | cresols | 2 |
| unknown | 15 | 65.1 | unknown | 12 |

Acid Wash Water Extraction
Starting Concentrations in Water

| Compound | mg/l |
|---|---|
| MNT | 0 |
| DNT | 1257 |
| cresols | 17 |
| unknown | 59 |

TABLE A

Toluene/water = 0.14 by volume
(toluene = 14.5 ml, water = 106.9 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 45 | 96.4 | DNT | 8935 |
| cresols | 6 | 64.7 | cresols | 81 |
| unknown | 5 | 91.5 | unknown | 398 |

TABLE B

Toluene/water = 0.62 by volume
(toluene = 40.0 ml, water = 65.0 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 0 | 100 | DNT | 2043 |
| cresols | 1 | 94.1 | cresols | 26 |
| unknown | 17 | 71.2 | unknown | 68 |

TABLE C

Toluene/water = 1.18 by volume
(toluene = 41.8 ml, water = 35.6 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 0 | 100 | DNT | 1071 |
| cresols | 2 | 88.2 | cresols | 13 |
| unknown | 54 | 8.5 | unknown | 4 |

TABLE D

Toluene/water = 2.39 by volume
(toluene = 57.9 ml, water = 24.2 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 0 | 100 | DNT | 525 |
| cresols | 2 | 88.2 | cresols | 6 |
| unknown | 7 | 88.1 | unknown | 22 |

Alkaline Wash Water Extraction
Starting Concentration in Water

| Compound | mg/l |
|---|---|
| MNT | 0 |
| DNT | 2033 |
| cresols | 4690 |
| unknown | 5055 |

TABLE A

Toluene/water = 0.13 by volume
(toluene = 13.3 ml, water = 101.0 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 25 | 98.8 | DNT | 15249 |
| cresols | 4518 | 3.7 | cresols | 1306 |
| unknown | 3953 | 21.8 | unknown | 8369 |

TABLE B

Toluene/water = 0.59 by volume
(toluene = 37.0 ml, water = 62.8 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 0 | 100 | DNT | 7365 |
| cresols | 3877 | 17.3 | cresols | 2945 |
| unknown | 3589 | 29.0 | unknown | 5311 |

TABLE C

Toluene/water = 1.11 by volume
(toluene = 55.0 ml, water = 49.5 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 0 | 100 | DNT | 1830 |
| cresols | 4101 | 12.6 | cresols | 530 |
| unknown | 3562 | 29.5 | unknown | 1344 |

TABLE D

Toluene/water = 2.39 by volume
(toluene = 79.2 ml, water = 33.1 ml)

| | Extracted water | | Concentrations in toluene (calculated) | |
|---|---|---|---|---|
| Compound | mg/l | % Extracted | Compound | mg/l |
| MNT | 0 | — | MNT | 0 |
| DNT | 0 | 100 | DNT | 850 |
| cresols | 4357 | 7.1 | cresols | 139 |
| unknown | 4002 | 20.8 | unknown | 440 |

The above results show that both MNT and DNT are efficiently extracted from wastewater and wash water streams using toluene. The lowest removal efficiencies observed (96–99%) corresponded to toluene:water volume ratios between 0.12–0.14 by volume (the lowest tested). At higher ratios, e.g., (toluene:water=0.60 to 2.4) removed 100% of the MNT and DNT was removed. The optimum ratio appears to be between 0.2 and 0.6 with the likely preferred ratio at the lower end of the range (0.2 to 0.3 by volume). At the lower ratios the required toluene volume is relatively low with respect to the total volume of toluene used as raw material in the DNT process ($\leq 10\%$) and, therefore, less toluene is put at risk in the event of a process upset or unforeseen problem.

The data also show that it is important that alkaline wash water is extracted last in the series and that the pH is adjusted to high enough values. The "dirty" toluene (water washed DNT) from the first two extraction steps contains cresols and other byproducts and, unless the last extraction step is conducted under alkaline conditions, the toluene can extract a large fraction of these oxidative byproducts. The products then would be recycled to the DNT possibly creating emulsions make necessary aqueous/organic phase separations difficult in the DNT process. A high pH, e.g., 8–9 in the alkaline extraction step may also "back-extract" organic byproducts from the toluene phase into the water phase, thus "cleaning" the toluene and isolating byproducts in a single stream which can be treated to destroy the environmentally objectionable compounds.

EXAMPLE 2

Effect of PH on Extraction of By-products from Toluene Extractions

Four experiments were conducted where "dirty" toluene was contacted with alkaline wash water at pH ranges ranging between 7 and 9. Both extraction efficiency (MNT, DNT) and by-product partitioning were measured for each condition. The results of those experiments are given below and the conclusions from them are: (1) pH has a significant effect on cleaning the "dirty" toluene (by-products in toluene decreases as pH increases), (2) DNT extraction efficiency increases marginally as pH increases, (3) Other (unknown) by-products in the toluene phase also decrease with increasing pH.

Toluene that was previously used to extract acid wastewater and wash waters was contacted with alkaline wash water at several pH levels. After separating the toluene from the aqueous phase, the water was analyzed for MNT, DNT, cresols and unknown compounds (estimated from area counts). The results are given below:

Initial conditions:

| Alkaline wash water | | "Dirty" toluene | |
|---|---|---|---|
| Compound | mg/l | Compound | mg/l |
| MNT | 0 | MNT | 2550 |
| DNT | 1675 | DNT | 19752 |
| cresols | 5087 | Cresols | 66 |
| unknown | 3120 | unknown | 38 |

Extraction #1: pH = 7.10, alkaline wash water = 72.2 ml,
toluene 30.3 ml (toluene/water = 0.42 by volume)

| | Extracted water | | Concentrations in toluene (calculated) | | |
|---|---|---|---|---|---|
| Compound | mg/l | % Extracted | Compound | mg/l | % Increase |
| MNT | 0 | — | MNT | 2550 | — |
| DNT | 49 | 97.1 | DNT | 23653 | 19.7 |
| cresols | 4185 | 17.7 | cresols | 2230 | 248 |
| Unknown | 2766 | 11.3 | unknown | 882 | 2221 |

Extraction #2: pH = 8.04, alkaline wash water = 72.6 ml,
toluene 30.3 ml (toluene/water = 0.42 by volume)

| | Extracted water | | Concentrations in toluene (calculated) | | |
|---|---|---|---|---|---|
| Compound | mg/l | % Extracted | Compound | mg/l | % Increase |
| MNT | 0 | — | MNT | 2550 | — |
| DNT | 31 | 98.1 | DNT | 23691 | 19.9 |
| cresols | 5662 | (11.3) | cresols | trace | — |
| unknown | 3481 | (11.6) | unknown | trace | — |

Extraction #3: pH = 8.38, alkaline wash water = 72.7 ml,
toluene 30.1 ml (toluene/water = 0.41 by volume)

| | Extracted water | | Concentrations in toluene (calculated) | | |
|---|---|---|---|---|---|
| Compound | mg/l | % Extracted | Compound | mg/l | % Increase |
| MNT | 0 | — | MNT | 2550 | — |
| DNT | 26 | 98.4 | DNT | 23735 | 20.2 |
| cresols | 5709 | (12.2) | cresols | trace | — |
| unknown | 3721 | (19.3) | unknown | trace | — |

Extraction #4: pH = 73.2, alkaline wash water = 73.2 ml,
toluene 30.7 ml (toluene/water = 0.42 by volume)

| | Extracted water | | Concentrations in toluene (calculated) | | |
|---|---|---|---|---|---|
| Compound | mg/l | % Extracted | Compound | mg/l | % Increase |
| MNT | 0 | — | MNT | 2550 | — |
| DNT | 24 | 98.6 | DNT | 23689 | 19.9 |
| cresols | 5453 | (7.2) | cresols | trace | — |
| unknown | 3619 | (16.0) | unknown | trace | — |

These data show the necessity of maintaining a pH>7. At pH=7, by-products are extracted into the toluene phase while at the higher pH (pH=9) nearly all the by-products are "back extracted" from the toluene into the water. DNT extraction into the toluene also improves somewhat (49 mg/l at pH=7, 24 mg/l at pH=9). The net effect is to dump nearly all the by-products found in the wastewater and wash waters into the alkaline wash water, which can be treated, and effect nearly total extraction of the DNT (~99%) from the wastewater and wash waters. It should also be observed that MNT initially in the "dirty" toluene remains in the toluene.

EXAMPLE 3

Batch Extraction of DNT Wash Water

Batch experiments were conducted where toluene was used to first extract DNT from weak acid wastewater, then reused to extract acid wash water, and, finally, alkaline wash water. The relative ratios of wastewater and wash waters approximate what would be expected in a typical nitration process. For this example the toluene:acid reconcentration water is 0.20 (the weak acid wastewater is the largest waste stream). The alkaline wash water had a final pH=7.5.

Step 1: weak acid wastewater extracted with clean toluene (water = 250 ml, toluene = 50 ml)

| Initial water concentrations | | Extracted water concentrations | | |
|---|---|---|---|---|
| Compound | mg/l | Compound | mg/l | % extracted |
| MNT | 162.6 | MNT | 0 | 100 |
| DNT | 1466.6 | DNT | 15.7 | 98.9 |
| cresols | 8.0 | Cresols | 2.1 | 73.8 |
| unknown | 29.9 | Unknown | 48.7 | — |

Step 2: acid wash water extracted with toluene separated from step 1 (water = 160 ml, toluene = 40 ml)

| Initial water concentrations | | Extracted water concentrations | | |
|---|---|---|---|---|
| Compound | mg/l | Compound | mg/l | % extracted |
| MNT | 0 | MNT | 0 | — |
| DNT | 3250.1 | DNT | 25.2 | 99.2 |
| cresols | 9.6 | Cresols | 2.1 | 78.1 |
| unknown | 85.0 | Unknown | 48.7 | 42.7 |

Step 3: alkaline wash water extracted with toluene separated from step 2 (water = 73 ml, toluene = 30 ml)

| Initial water concentrations | | Extracted water concentrations | | |
|---|---|---|---|---|
| Compound | mg/l | Compound | mg/l | % extracted |
| MNT | 0 | MNT | 0 | — |
| DNT | 1977.5 | DNT | 16.5 | 99.2 |
| cresols | 4053.9 | Cresols | 3835.2 | (5.4) |
| unknown | 4270.4 | Unknown | 3819.9 | (10.5) |

It should be noted that cresols and other by-products (unknowns) would be present in higher concentrations if the final pH were maintained at higher levels, as previously demonstrated.

What is claimed is:

1. In a process for the production of dinitrotoluene which comprises contacting toluene with a mixture of nitric and sulfuric acid under conditions for effecting dinitration and generating three acidic aqueous streams contaminated with residual levels of mononitrotoluene, dinitrotoluene and organic by-products, said acidic aqueous streams formed in the purification of the dinitrotoluene reaction product and concentration of spent sulfuric acid, one wastewater stream generated from spent sulfuric acid and referred to as weak acid wastewater; one from the washing of the dinitrotoluene reaction product and referred to as acid wash water stream, and one resulting from alkaline washing of the dinitrotoluene reaction product and referred to as alkaline wash water stream; the improvement which comprises the steps:

(a) initially extracting mononitrotoluene, dinitrotoluene and organic by-products from at least one stream selected from the group consisting of the weak acid wastewater stream and acid wash water stream by contacting the stream with toluene and thereby generating an organic phase and an aqueous phase;

(b) separating the thus formed organic phase from the aqueous phase;

(c) extracting mononitrotoluene, dinitrotoluene and organic by-products from the alkaline wash water stream by contacting said stream with the organic phase generated in step (a) and thereby generating a toluene/dinitrotoluene organic layer and an extracted alkaline wash water fraction; and, (d) separating the toluene/dinitrotoluene organic layer from the extracted alkaline wash water fraction.

2. The process of claim 1 wherein the ratio of toluene to wastewater and wash water for the three streams is from 0.1 to 2.5 volume parts toluene per volume part total wastewater and wash water.

3. The process of claim 2 wherein the extracting in step(c) is carried out at a pH of from 8 to 9.

4. The process of claim 1 wherein both weak acid wastewater and acid wash water are extracted with toluene in the initial extraction.

5. The process of claim 4 wherein the volume parts toluene per volume part wastewater and wash water is from 0.2 to 0.6:1.

6. The process of claim 5 wherein the weak acid wastewater is initially extracted with toluene generating an organic phase and an aqueous phase, the phases separated, and the resulting organic phase, then, employed for extracting the acid wash water thereby generating a second organic phase comprised of toluene and DNT and a second aqueous phase.

7. The process of claim 5 wherein the volume parts toluene per volume part wash water is from 0.2 to 0.3:1.

8. The process of claim 5 wherein the extraction process is effected in inline static mixers.

* * * * *